(12) United States Patent
Liang et al.

(10) Patent No.: US 9,719,912 B2
(45) Date of Patent: Aug. 1, 2017

(54) CROSS-CUT TESTER

(71) Applicants: SHENZHEN FUTAIHONG PRECISION INDUSTRY CO., LTD., Shenzhen (CN); FIH (Hong Kong) Limited, Kowloon (HK)

(72) Inventors: Jung-Chen Liang, New Taipei (TW); Guo-Zeng Zheng, Shenzhen (CN); Jun-Wu Hu, Shenzhen (CN); Lei Cui, Shenzhen (CN)

(73) Assignees: SHENZHEN FUTAIHONG PRECISION INDUSTRY CO., LTD., Shenzhen (CN); FIH (HONG KONG) LIMITED, Kowloon (HK)

( * ) Notice: Subject to any disclaimer, the term of this patent is extended or adjusted under 35 U.S.C. 154(b) by 239 days.

(21) Appl. No.: 14/526,059

(22) Filed: Oct. 28, 2014

(65) Prior Publication Data

US 2016/0047736 A1   Feb. 18, 2016

(30) Foreign Application Priority Data

Aug. 12, 2014  (CN) .......................... 2014 1 0394748

(51) Int. Cl.
*G01N 19/04* (2006.01)
*B26B 5/00* (2006.01)
*B26B 29/02* (2006.01)

(52) U.S. Cl.
CPC ............. *G01N 19/04* (2013.01); *B26B 5/002* (2013.01); *B26B 5/008* (2013.01); *B26B 29/02* (2013.01)

(58) Field of Classification Search
CPC ......... B26B 29/02; B26B 5/002; B26B 5/008; B26B 5/001; B26B 29/06; B26B 5/00; B26B 3/04; B26B 11/00; B26B 1/00; B26B 1/042; B26B 1/08; B26B 27/00; B26B 3/00; B26B 5/005; G01N 19/04
See application file for complete search history.

(56) References Cited

U.S. PATENT DOCUMENTS

| | | | | | |
|---|---|---|---|---|---|
| 2,137,333 | A | * | 11/1938 | Colburn | B44B 11/02 30/164.9 |
| 2,464,206 | A | * | 3/1949 | Becker | B26B 3/04 30/304 |
| 3,270,368 | A | * | 9/1966 | Cook, Sr. | A22C 25/02 30/304 |
| 3,389,463 | A | * | 6/1968 | Gerek | G01N 19/04 30/164.9 |
| 3,488,843 | A | * | 1/1970 | Tims, Jr. | B26B 5/00 30/162 |

(Continued)

FOREIGN PATENT DOCUMENTS

CN     101908743 A     12/2010

*Primary Examiner* — Daniel S Larkin
*Assistant Examiner* — Anthony W Megna Fuentes
(74) *Attorney, Agent, or Firm* — Steven Reiss

(57) ABSTRACT

A cross-cut tester includes a handle with a receiving cavity, and a plurality of blades received in the receiving cavity. One end of the handle defines an opening. The cross-cut tester further includes a plurality of gaskets received in the receiving cavity. The gaskets and the blades are positioned one-by-one, and are detachably fixed in the receiving cavity. The cross-cut tester of the present disclosure can effectively improve the efficiency of drawing lines and reduce the cost.

14 Claims, 6 Drawing Sheets

(56) References Cited

U.S. PATENT DOCUMENTS

| | | | | |
|---|---|---|---|---|
| 3,724,071 A | * | 4/1973 | Hurtubise | B26B 5/008 30/287 |
| 3,911,575 A | * | 10/1975 | Anesi | B26B 25/005 30/164.9 |
| 4,288,921 A | * | 9/1981 | Rhynes | A21C 11/12 30/304 |
| 4,472,879 A | * | 9/1984 | Sizemore, Jr. | B26B 3/03 30/287 |
| 4,578,865 A | * | 4/1986 | Keller | B26B 5/008 30/162 |
| 5,337,481 A | * | 8/1994 | Mears | B26B 5/008 30/162 |
| 5,911,808 A | * | 6/1999 | Mendenhall | B26D 1/48 30/117 |
| D418,036 S | * | 12/1999 | Shearer | D8/98 |
| 6,308,422 B1 | * | 10/2001 | MacDonald | B26B 3/04 30/125 |
| 6,550,143 B1 | * | 4/2003 | Derome | B26B 5/001 30/162 |
| 6,722,044 B2 | * | 4/2004 | Timidaiski | B26B 5/005 30/329 |
| 6,887,250 B1 | * | 5/2005 | Dority | A61B 17/3213 30/305 |
| 8,011,103 B2 | * | 9/2011 | Blum | A21C 11/106 30/299 |
| 8,065,945 B2 | * | 11/2011 | Kobayashi | A61B 10/02 30/173 |
| 8,322,531 B2 | * | 12/2012 | Miller | B65D 73/0014 206/493 |
| 8,438,737 B2 | * | 5/2013 | Lo | B26B 3/04 30/114 |
| 8,572,854 B2 | * | 11/2013 | Estoppeij | B26B 3/04 30/299 |
| 8,635,781 B2 | * | 1/2014 | Fischer | B26B 3/04 30/304 |
| 9,333,643 B2 | * | 5/2016 | Brallier | B25H 7/045 |
| 2001/0034932 A1 | * | 11/2001 | MacDonald | B26B 3/04 29/428 |
| 2004/0031160 A1 | * | 2/2004 | Timidaiski | B26B 5/005 30/329 |
| 2004/0250423 A1 | * | 12/2004 | Yu | B23D 61/12 30/123 |
| 2005/0229405 A1 | * | 10/2005 | Endres | B26B 5/008 30/305 |
| 2006/0185488 A1 | * | 8/2006 | Short | B26D 1/553 83/581.1 |
| 2006/0207403 A1 | * | 9/2006 | Moss | B26B 3/04 83/870 |
| 2007/0249477 A1 | * | 10/2007 | Mueller | B26B 3/08 493/459 |
| 2007/0294898 A1 | * | 12/2007 | Beltran | B26B 5/008 30/307 |
| 2009/0144987 A1 | * | 6/2009 | Mills | B26B 3/04 30/173 |
| 2010/0212518 A1 | * | 8/2010 | Sherrill | B26D 1/04 99/537 |
| 2013/0074671 A1 | * | 3/2013 | Tamamura | B26B 5/001 83/582 |
| 2013/0192069 A1 | * | 8/2013 | Reibold | B26B 1/10 30/295 |
| 2013/0239415 A1 | * | 9/2013 | Wagner | B26B 5/002 30/162 |

* cited by examiner

CROSS-CUT TESTER

FIELD

The subject matter herein generally relates to a cross-cut tester, and in particular to a cross-cut tester for adhesion testing of decorative painted film.

BACKGROUND

A cross-cut tester is mainly used to test an adhesion of decorative painted films. The cross-cut tester can carve crosswise on the surface of the film along vertical and horizontal directions, and the film can form many separate grids. A piece of tape can be covered over the separate grids, and the tape is quickly pulled up. The adhesion of the film can be determined by the number of the grids peeling off the film.

BRIEF DESCRIPTION OF THE DRAWINGS

Implementations of the present technology will now be described, by way of example only, with reference to the attached figures.

DETAILED DESCRIPTION

Figure 1:
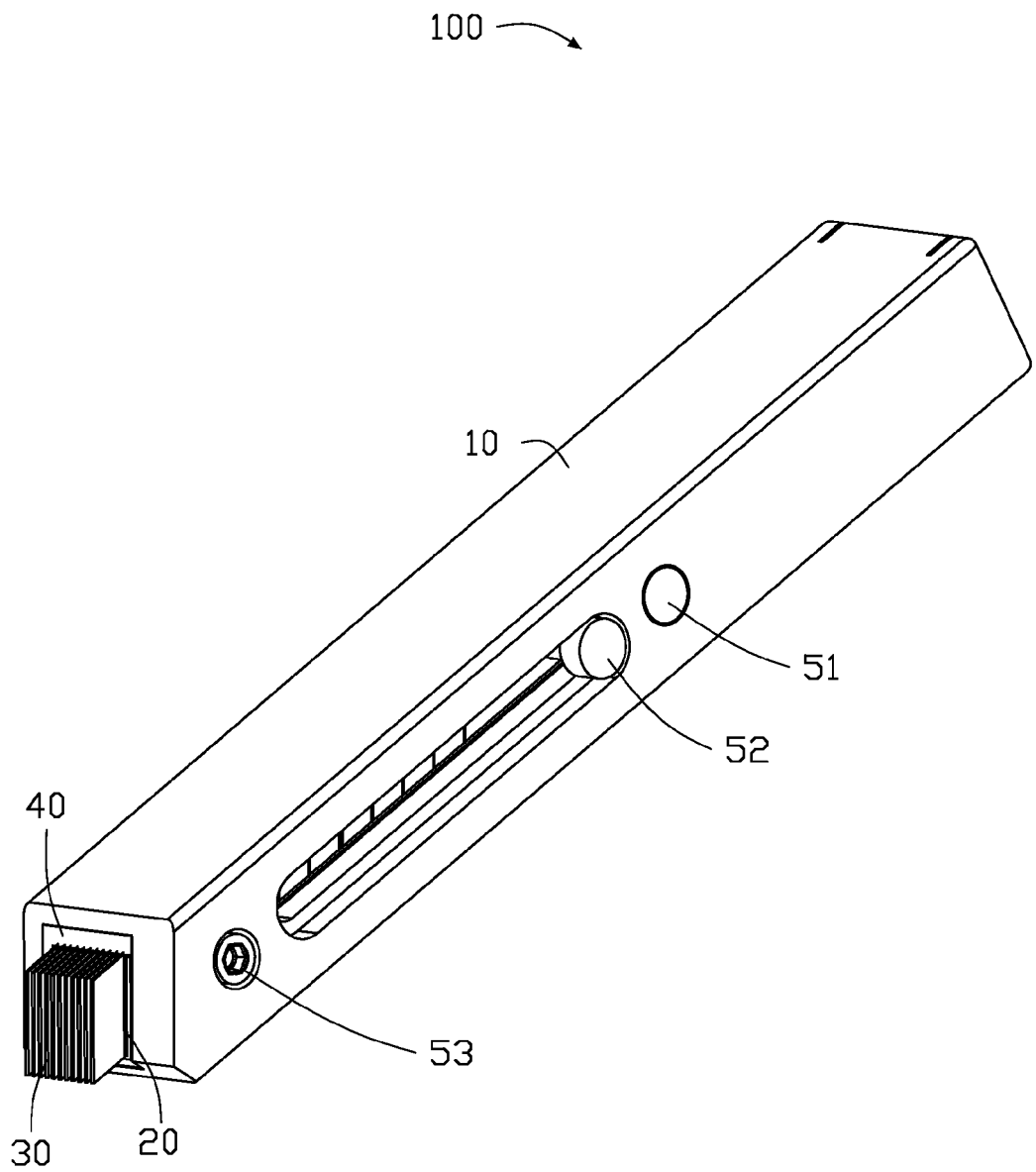
FIG. 1 is an isometric view of an embodiment of a cross-cut tester.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented.

The term "outside" refers to a region that is beyond the outermost confines of a physical object. The term "substantially" is defined to be essentially conforming to the particular dimension, shape, or other feature that the term modifies, such that the component need not be exact. For example, "substantially cylindrical" means that the object resembles a cylinder, but can have one or more deviations from a true cylinder. The term "comprising" when utilized, means "including, but not necessarily limited to"; it specifically indicates open-ended inclusion or membership in the so-described combination, group, series and the like.

FIG. 1 illustrates an embodiment of a cross-cut tester 100. The cross-cut tester 100 can include a handle 10, a plurality of gaskets 20, a plurality of blades 30, and a position limiting frame 40. The handle 10 can be substantially hollow and columnar. The gaskets 20 can be received in the handle 10. A portion of the blades 30 can be received in the handle 10. The blades 30 and the gaskets 20 can be alternately positioned one-by-one. The position limiting frame 40 can be positioned at one end of the handle 10, and can prevent the blades 30 from moving. The blades 30 can be fixed in the handle 10 with a first screw 51. The gaskets 20 can be fixed in the handle 10 with a second screw 52. The position limiting frame 40 can be fixed in the handle 10 with a third screw 53. A distance between the blades 30 can be the same, and the cross-cut tester 100 can draw many uniform lines at one time.

Figure 2:
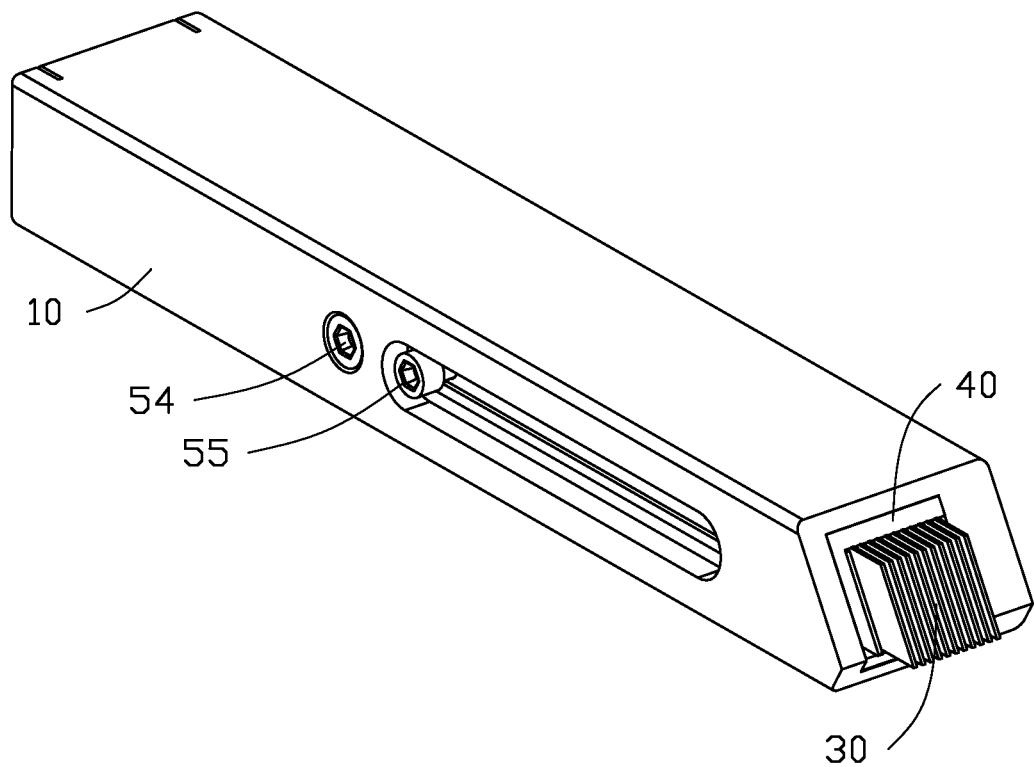
FIG. 2 is an isometric view of the cross-cut tester as shown in FIG. 1 from another perspective.

FIG. 2 illustrates that one end of the first screw 51 (as shown in FIG. 1) can be locked by a nut 54. Thus, the blades 30 can be detachably mounted in the handle 10. One end of the second screw 52 (as shown in FIG. 1) can be locked by a nut 55. Thus, the gaskets 20 can be detachably mounted on the handle 10.

Figure 3:
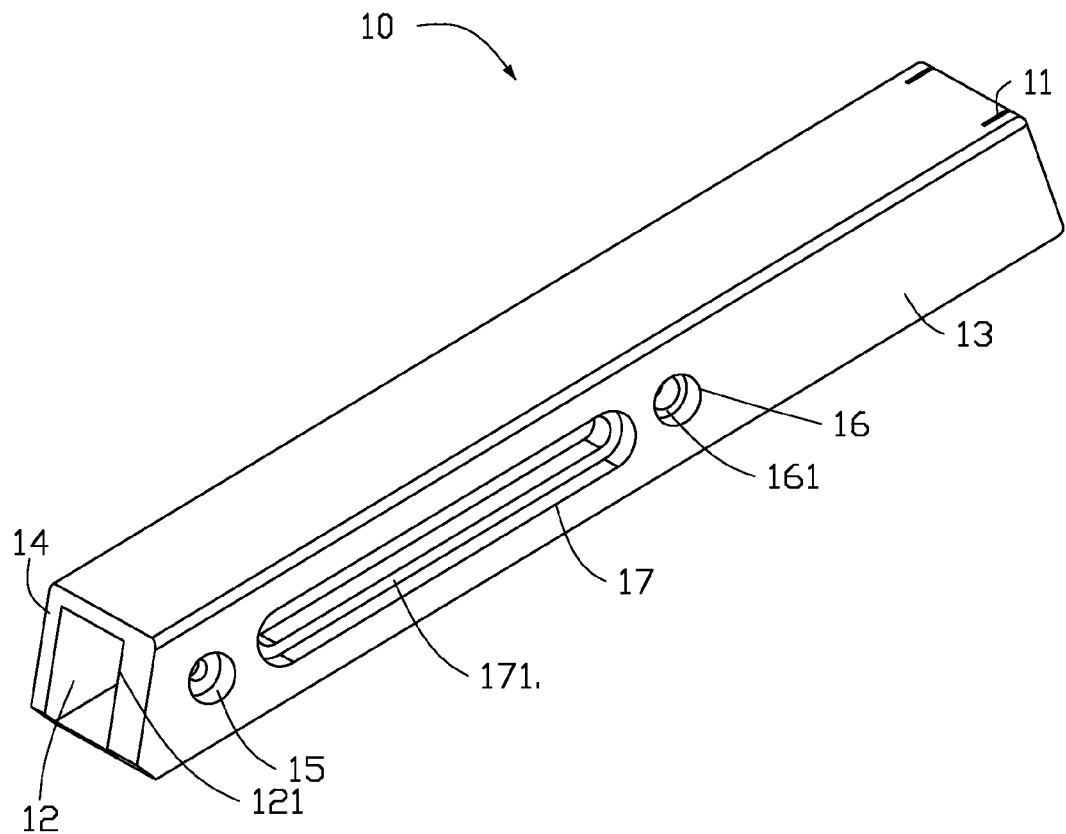
FIG. 3 is an isometric view of a handle of the cross-cut tester as shown in FIG. 1.

FIG. 3 illustrates that at least one groove 11 can be defined in one end of the handle 10 which can be sealed. A blunt part of the blades 30 (as shown in FIG. 1) can be positioned in the groove 11, and can be broken by the groove 11. A receiving cavity 12 can be defined in the handle 10. The receiving cavity 12 can be configured to receive the gaskets 20 (as shown in FIG. 1) and the blades 30. The other end of the handle 10 can define an obliquely arranged opening 121. An oblique angle of the opening 121 can be the substantially the same as an angle of a front end of each blade 30. The handle 10 can further include a first sidewall 13 and a second sidewall 14, and the first sidewall 13 and the second sidewall 14 are relatively arranged.

A position of the first sidewall 13 adjacent to the opening 121 can define a screw hole 15, the third screw 53 can be screwed into the handle 10, and can be resisted against the position limiting frame 40. A through hole 16 can be defined in a position of the handle 10 away from the opening 121. The through hole 16 can pass through the first sidewall 13 and the second sidewall 14. The through hole 16 can include a resisting portion 161. The resisting portion 161 can be located in the through hole 16 adjacent to the receiving cavity 12. The resisting portion 161 can be substantially a ring, and can be configured to resist against the first screw 51 (as shown in FIG. 1). A substantially long sliding groove 17 can be defined in a substantially central position of the handle 10. An edge of the sliding groove 17 can include a resisting portion 171. The resisting portion 171 can be located in the sliding groove 17 adjacent to the receiving cavity 12. The resisting portion 171 can be substantially ring shaped, and can be configured to resist against the second screw 52 (as shown in FIG. 1). The second screw 52 can resist against the different positions of the sliding groove 17.

Figure 4:
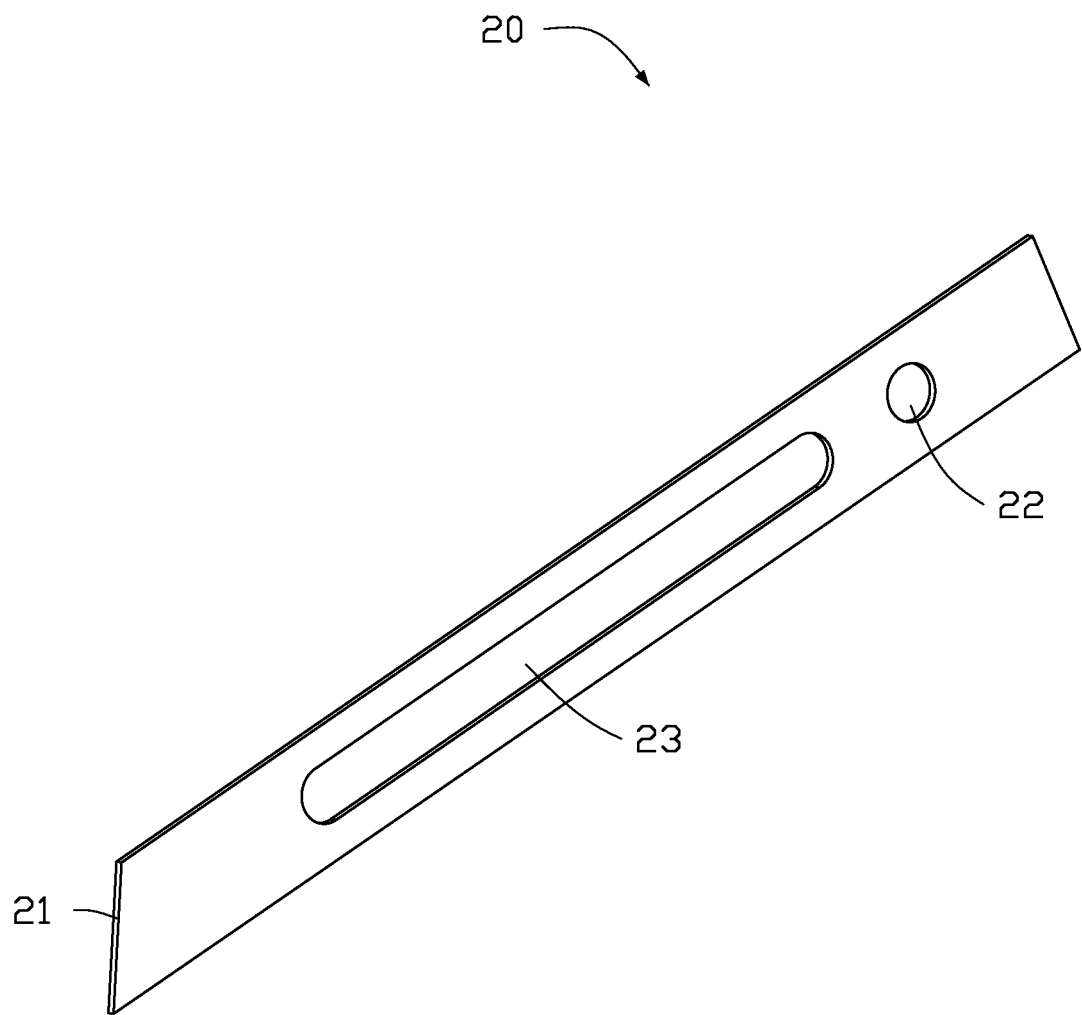
FIG. 4 is an isometric view of a gasket of the cross-cut tester as shown in FIG. 1.

FIG. 4 illustrates that each gasket 20 can be substantially a parallelogram. One end of the gasket 20 can include a bevel 21, and a shape of the bevel 21 can be the same as a shape of the front end of the blade 30. The other end of the gasket 20 can define a fixing hole 22. The first screw 51 (as shown in FIG. 1) can pass through the fixing hole 22 to fix the gasket 20 in the handle 10. A substantially central position of the gasket 20 can define a fixing groove 23. A shape of the fixing groove 23 can be substantially the same as a shape of the sliding groove 17 (as shown in FIG. 3). The second screw 52 (as shown in FIG. 1) can pass through the fixing groove 23, and the blades 30 can be fixed to the different positions of the fixing groove 23.

Figure 5:
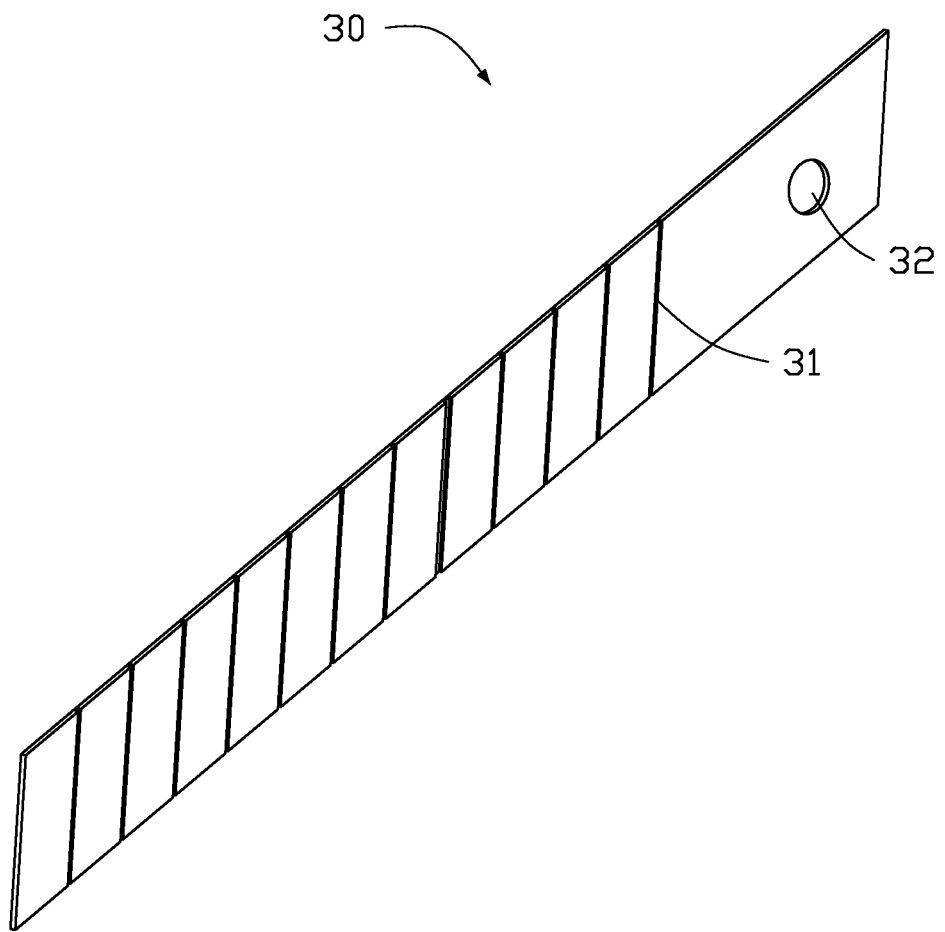
FIG. 5 is an isometric view of a blade of the cross-cut tester as shown in FIG. 1.

FIG. 5 illustrates that each blade 30 can be substantially a parallelogram. The blade 30 can include a plurality of creases 31. When the blade 30 is blunt, the blunt part of the blade 30 can be easily broken along the creases 31. One end of the blade 30 can define a fixing hole 32. The second screw 52 (as shown in FIG. 1) can pass into the sliding groove 17 (as shown in FIG. 3), the fixing groove 23 (as shown in FIG. 4) and the fixing hole 32, and can pass through the other sliding groove 17. Thus, each gasket 20 can resist against each blade 30, and the blades 30 can be fixed between the gaskets 20.

Figure 6:
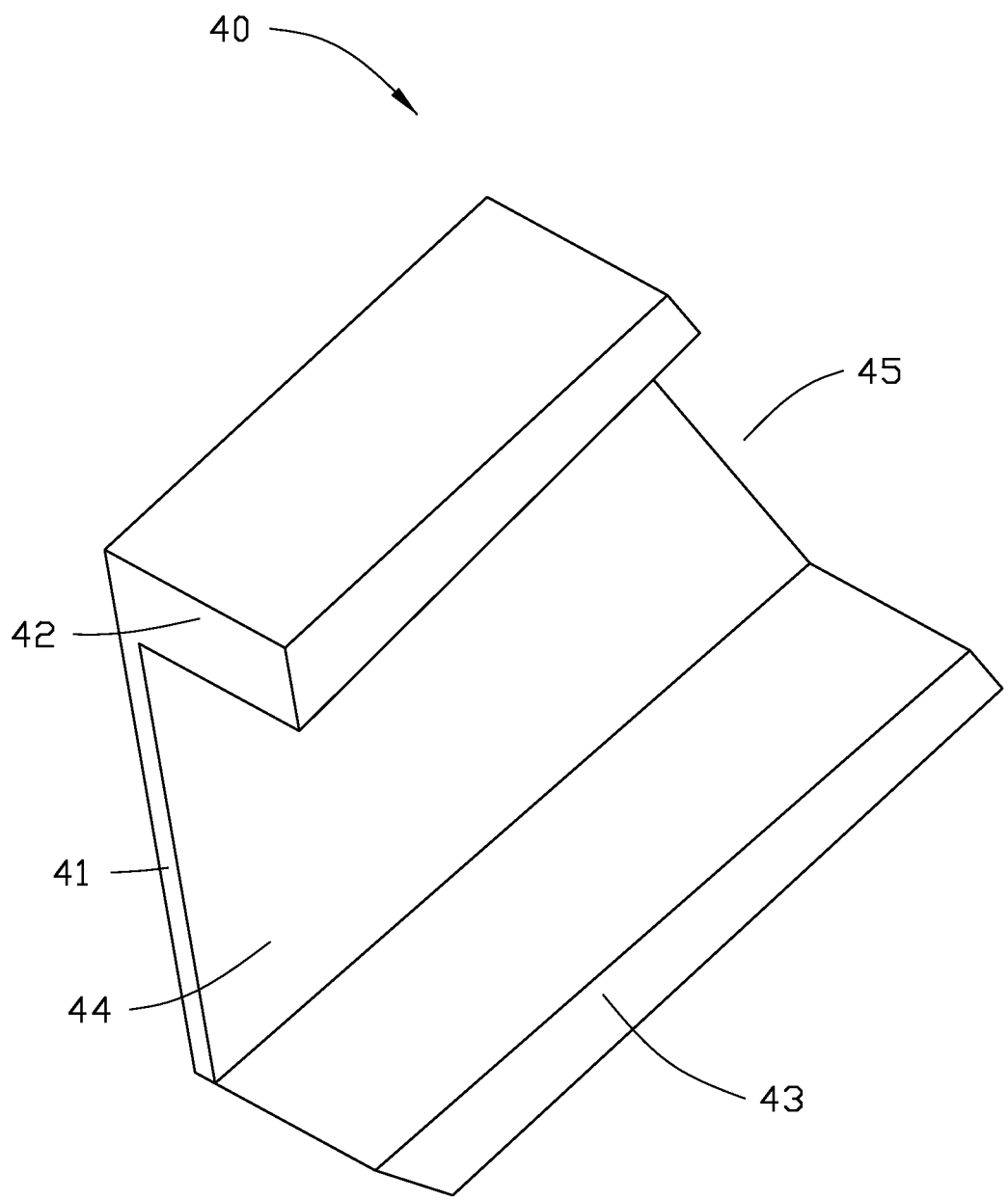
FIG. 6 is an isometric view of a position limiting frame of the cross-cut tester as shown in FIG. 1.

FIG. 6 illustrates that the position limiting frame 40 can include a first plate 41, a second plate 42, and a third plate 43. The second plate 42 and the third plate 43 can extend along a vertical direction of the first plate 41. The first plate 41, the second plate 42 and the third plate 43 can combine to form a front opening 44 and a back opening 45. An oblique angle of the front opening 44 can be the substantially the same as an angle of the opening 121 (as shown in FIG. 3). A size of the front opening 44 can be smaller than a size of the back opening 45 to prevent the blades 30 (as shown in FIG. 5) from moving. Thus, lines drawn by the blades 30 can be equal. The position limiting frame 40 can be mounted in the opening 121, and the first plate 41 can be attached to the second sidewall 14 (as shown in FIG. 3). The third screw 53 (as shown in FIG. 1) can pass through the screw hole 15 (as shown in FIG. 3) and resist against the blades 30 and the gaskets 20 (as shown in FIG. 1) to the first plate 41. Thus, the blades 30 can be partly and steady surrounded by the position limiting frame 40. A standard width of each blade 30 can be about 9.0±0.1 mm, and the width of some blades 30 can be about 9.24 mm. Therefore, a width of the front opening 44 can be 9.12 mm or 9.26 mm allowing the blade 30 be held in the position limiting frame 40.

The embodiments shown and described above are only examples. Many details are often found in the art such as the other features of a cross-cut tester 100. Therefore, many such details are neither shown nor described. Even though numerous characteristics and advantages of the present technology have been set forth in the foregoing description, together with details of the structure and function of the present disclosure, the disclosure is illustrative only, and changes may be made in the details, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A cross-cut tester comprising:
   a handle comprising a receiving cavity;
   a plurality of gaskets, the gaskets completely received in the receiving cavity; and
   a plurality of blades, a portion of the blades received in the receiving cavity;
   wherein one end of the handle comprises an opening; wherein the gaskets and the blades are alternately arranged and are detachably mounted in the receiving cavity; and wherein the blades extend out of the receiving cavity through the opening; and
   wherein a central position of each gasket defines a lengthwise fixing groove.

2. The cross-cut tester of claim 1, wherein the cross-cut tester further comprises a position limiting frame received in the receiving cavity, and wherein the position limiting frame is arranged adjacent to the opening.

3. The cross-cut tester of claim 2, wherein the position limiting frame comprises a first plate, a second plate, and a third plate; and wherein the second plate and the third plate extends along a vertical direction of the first plate.

4. The cross-cut tester of claim 3, wherein the first plate, the second plate, and the third plate are combined to form a front opening and a back opening; and wherein an area of the front opening is smaller than an area of the back opening.

5. The cross-cut tester of claim 4, wherein the opening of the handle and the front opening of the position limiting frame are obliquely arranged, and wherein an oblique angle of the front opening is the same as an angle of the opening.

6. The cross-cut tester of claim 4, wherein the position limiting frame is mounted in the opening, and wherein the opening of the handle and the front opening of the position limiting frame are coplanar.

7. The cross-cut tester of claim 4, wherein the position limiting frame partly surrounds the blades, and wherein the blades extend out of the position limiting frame through the front opening and the back opening.

8. The cross-cut tester of claim 2, wherein the position limiting frame partly surrounds the blades to prevent movements of the blades.

9. The cross-cut tester of claim 1, wherein the handle further comprises a first sidewall and a second sidewall; and wherein the first sidewall and the second sidewall are arranged to face each other.

10. The cross-cut tester of claim 9, wherein a position of the first sidewall adjacent to the opening defines a screw hole; and wherein a screw can screw into the screw hole.

11. The cross-cut tester of claim 9, wherein a position of the handle away from the opening defines a through hole; wherein the through hole is defined through the first sidewall and the second sidewall; and wherein the through hole comprises a resisting portion adjacent to the receiving cavity.

12. The cross-cut tester of claim 9, wherein a central position of the handle defines a lengthwise sliding groove; wherein the sliding groove is defined through the first sidewall and the second sidewall; and wherein the sliding groove comprises a resisting portion adjacent to the receiving cavity.

13. The cross-cut tester of claim 1, wherein one end of each gasket comprises a bevel and the other end of each gasket defines a fixing hole.

14. The cross-cut tester of claim 1, wherein one end of the handle away from the opening defines at least one groove.

* * * * *